(12) United States Patent
Mills (10) Patent No.: US 7,086,924 B2
(45) Date of Patent: Aug. 8, 2006

(54) MODULAR CAVITY NESTING FOR HYMENOPTERA

(76) Inventor: Jerry L. Mills, 144 S. Slope Rd., Emmett, ID (US) 83617

( * ) Notice: Subject to any disclaimer, the term of this patent is extended or adjusted under 35 U.S.C. 154(b) by 0 days.

(21) Appl. No.: 11/034,430

(22) Filed: Jan. 11, 2005

(65) Prior Publication Data

US 2006/0154565 A1    Jul. 13, 2006

(51) Int. Cl.
*A01K 47/00* (2006.01)
*A01K 29/00* (2006.01)
(52) U.S. Cl. ............................................. 449/4; 119/6.5
(58) Field of Classification Search .................. 449/3, 449/4, 29, 30, 32, 34; 119/6.5, 6.6, 431
See application file for complete search history.

(56) References Cited

U.S. PATENT DOCUMENTS

| | | | |
|---|---|---|---|
| 502,486 A | 8/1893 | Dewey | 449/36 |
| 3,191,199 A | 6/1965 | Barnes | 449/4 |
| 3,267,497 A | 8/1966 | Dority | 449/4 |
| 3,936,894 A | 2/1976 | Barber | 449/4 |
| 4,319,371 A | 3/1982 | Wiederrich | 449/4 |
| 4,491,994 A * | 1/1985 | Youssef | 449/4 |
| 4,628,558 A | 12/1986 | Pederson | 449/4 |
| 4,765,007 A | 8/1988 | McCarthy | 449/4 |
| 4,787,108 A | 11/1988 | Norman | 449/1 |
| 4,799,944 A * | 1/1989 | Dixon et al. | 55/446 |
| 5,372,535 A | 12/1994 | Mills | 499/4 |
| 5,403,226 A | 4/1995 | Trafford | 449/4 |
| 5,591,063 A * | 1/1997 | McCarthy | 449/4 |
| 5,618,220 A | 4/1997 | Mills | 449/4 |

* cited by examiner

Primary Examiner—Son T. Nguyen
(74) Attorney, Agent, or Firm—Joseph W. Holland (57) ABSTRACT

A modular nest including a backing member including a pair of generally opposing leafs connected to a spine and a removable nesting substrate including a plurality of grooves formed on a first face, the plurality of grooves forming a plurality of nesting cavities when the nesting substrate is folded along a line substantially perpendicular to an axis of one of the plurality of grooves, the nesting substrate removably inserted between the pair of generally opposing leafs of the backing member. A nest closure member is adapted for selective engagement for holding the backing member and the nesting substrate in a closed position wherein the plurality of grooves form the plurality of nesting cavities and an open position wherein the nesting substrate is laid open and the plurality of grooves are exposed.

19 Claims, 7 Drawing Sheets

MODULAR CAVITY NESTING FOR HYMENOPTERA

BACKGROUND OF THE INVENTION

1. Technical Field

This invention relates generally to management systems and nesting for hymenoptera, and more particularly to a modular nesting system for hymenoptera including leafcutter bees and orchard bees, (family Megachilidae).

2. Background

Management of leafcutter bees and orchard bees for pollination of crops has had a significant effect on the commercial success of various crops. Cavity nesting for hymenoptera including leafcutter bees and orchard bees has been developed by simply drilling a plurality of holes in a short length of lumber, for instance a length of a "4×6". Cavity nesting has also been developed employing Styrofoam blocks, having a plurality of holes drilled through a cross-section. Any of these systems suffer from drawbacks recognized at the time larvae, are removed from the cavities. In either case, because of the various methods commonly employed to remove the larvae, including drilling operations, many larvae may be destroyed in the process, thereby lowering yields. Additionally, certain materials or configurations of materials may prove difficult to sterilize and/or re-utilize for nesting. Additionally, any given material may be more or less acceptable to a particular hymenoptera for nesting.

U.S. Pat. Nos. 5,372,535 and 5,618,220 to Mills both entitled Leafcutter Bee Management System Including a Laminate Bee Board, and which are incorporated by reference herein, disclose a bee nest made from a plurality of bee board laminates held in close side by side relation by a permanent, flexible and lightproof backing material. The nest includes a closure for releasably opening and closing the nest at the front edges of the laminates. The '535 and '220 patents disclose a plurality of beeboard laminates formed out of wood, polystyrene or other suitable material. In practice it has been observed that wood may be too costly for widespread use and polystyrene may in fact not be favored by bees and other hymenoptera. Additionally, the feature of a permanent, flexible and lightproof backing material leads to a situation wherein, in the event that one or more of the laminates are damaged or otherwise require replacement, it may be that the entire nest is discarded rather than attempting to repair one or more damaged laminates due to the permanent binding. Additionally, it has been observed that while wood is durable it is relatively heavy. Additionally, it has been observed that nests formed of polymers or materials including polymers may be lighter and easier to handle than wood, in some cases they tend not to be as durable as wood products, in others cases they appear not to be preferred by the insects for nesting.

It may be desirable to provide a low cost modular cavity nesting for hymenoptera including leafcutter bees that is economical to produce and is manufactured of a material having adequate strength, while being preferably lighter than a similar structure formed of wood. Additionally, it may be desirable to provide modular cavity nesting for hymenoptera that is acceptable to the insects. Additionally, it may be desirable to provide modular cavity nesting for hymenoptera including non-permanent nesting substrates that are removable and replaceable. Additionally, it would be desirable to provide a modular nest which is adaptable for husbandry for both education/research and bee management purposes.

Therefore, one objective of the present invention is to provide a low cost modular cavity nesting for hymenoptera including leafcutter bees that is economical to produce and is manufactured of a material having adequate strength, while being preferably lighter than a similar structure formed of wood. An additional object of the present invention is to provide modular cavity nesting for hymenoptera that is manufactured of a material that is acceptable to the insects. An additional object of the present invention is to provide modular cavity nesting for hymenoptera including non-permanent nesting substrates that are removable and replaceable. Additionally, an objective of the present invention is to provide a modular nest which is adaptable for husbandry for both education/research and bee management purposes.

SUMMARY OF THE INVENTION

The present invention is directed to a nesting substrate for a modular cavity nest for hymenoptera including a plurality of grooves formed on a first face, the plurality of grooves formed on a face of the nesting substrate forming a plurality of nesting cavities when the nesting substrate is folded along a line substantially perpendicular to an axis of one of the plurality of grooves, each of the plurality of nesting cavities including a blind end when the nesting substrate is folded along a line substantially perpendicular to an axis of one of the plurality of grooves. The present invention is also directed to a modular nest including a backing member having a spine and a pair of generally opposing leafs connected to the spine. The modular nest also includes a nesting substrate including a plurality of grooves formed on a first face, the plurality of grooves forming a plurality of nesting cavities when the nesting substrate is folded along a line substantially perpendicular to an axis of one of the plurality of grooves, the nesting substrate removably inserted between the pair of generally opposing leafs of the backing member. A nest closure member is adapted for selective engagement for holding the backing member and the nesting substrate in a closed position wherein the plurality of grooves form the plurality of nesting cavities and an open position wherein the nesting substrate is laid open and the plurality of grooves are exposed.

In a preferred embodiment of the invention a plurality of nesting substrates are removably insertable against a plurality of backing members in an interleafed arrangement. In the preferred embodiment, adjacent backing members are connected one to the next and a nesting substrate is inserted between a pair of adjacent foldable leafs of a backing members. Alternately, the backing members may be formed as a molded element wherein a plurality of leafs extend from a common spine and the plurality of nesting substrates are removably insertable between the plurality of leafs in an interleafed arrangement.

DETAILED DESCRIPTION

Figure 1:
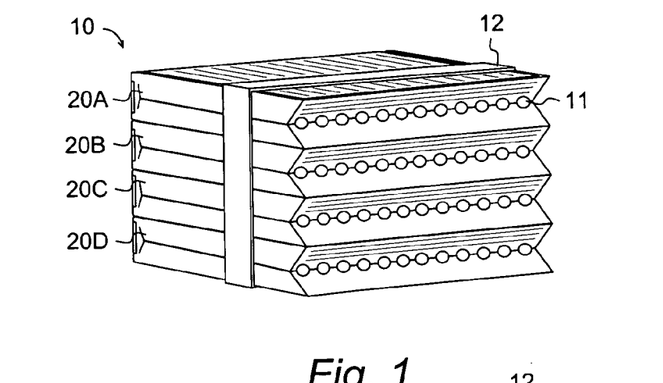
FIG. 1 is a representative perspective view of a modular cavity nest according to a preferred embodiment of the present invention.

Referring to FIG. 1 modular cavity nest 10 is shown to advantage. As shown, modular cavity nest 10 includes a plurality of nesting substrates 20A–20D. When configured as shown, that is folded in a closed position, the plurality of nesting substrates 20A–20D form a plurality of nesting cavities, cavity 11 being largely typical of any of the plurality of nesting cavities. Nest closure member 12 provides a means for maintaining the plurality of nesting substrates 20A–20D in a closed position during nesting. Nest closure member 12 may be configured as an elastic band or as a strap including a cinching member. Alternately, a closure member may be configured as a string and button type closure, hook and loop fabric or any of a variety of devices that may be used to selectively secure the plurality of nesting substrates, shown generally as 20 in a closed position.

Figure 2:
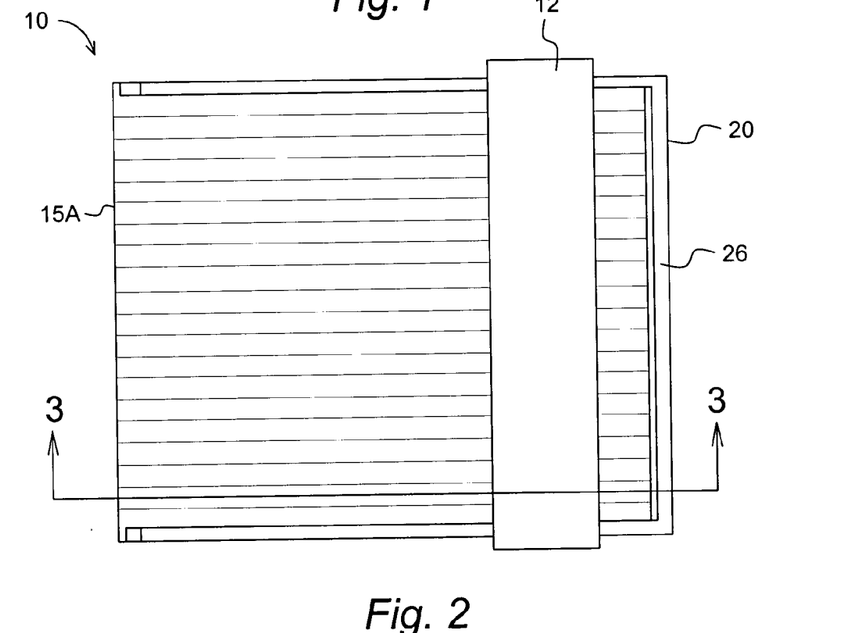
FIG. 2 is a representative top view of a modular cavity nest according to a preferred embodiment of the present invention.
Figure 3:
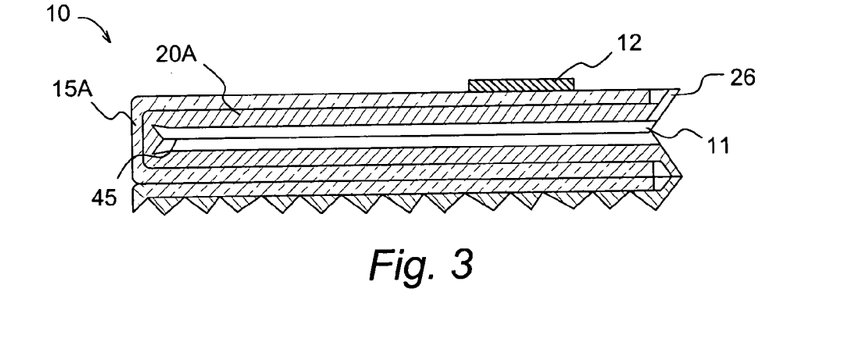
FIG. 3 is a representative side cutaway view of a modular cavity nest according to a preferred embodiment of the present invention.

Referring to FIG. 2, a top view of modular cavity nest 10 is shown including nesting substrate 20 and a portion of nest closure member 12. Backing member 15A is shown positioned within flange 26 of nesting substrates 20. FIG. 3 is a cross-sectional side view taken through nesting substrate 20A of modular cavity nest 10. FIG. 3 shows backing member 15A positioned within flange 26 of nesting substrate 20A. Cavity 11 includes blind end 45 formed when nesting substrate 20A is folded to a closed position as shown. A portion of nest closure member 12 is shown positioned against backing member 15A.

Figure 4:
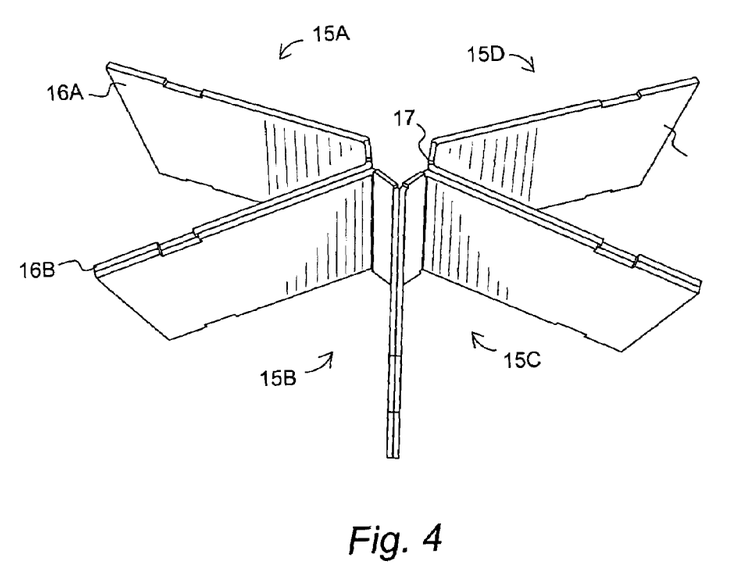
FIG. 4 is a representative perspective view of a plurality of backing members according to a preferred embodiment of the present invention.
Figure 5:
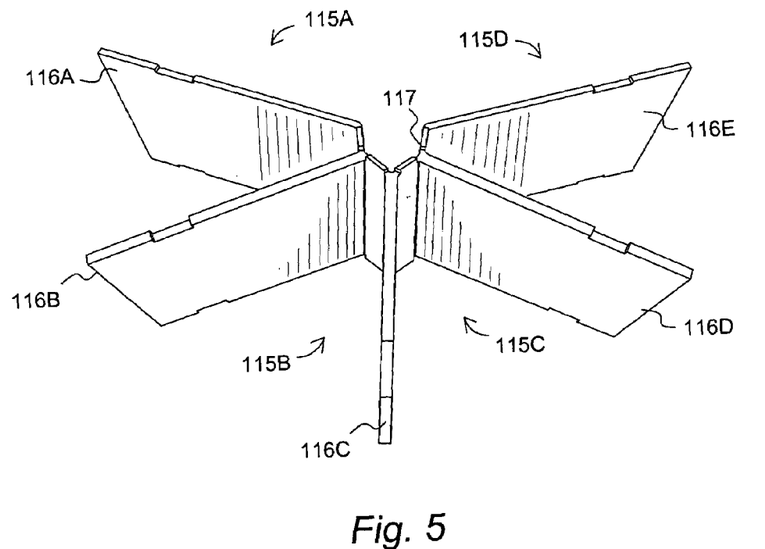
FIG. 5 is a representative perspective view of a plurality of backing members according to an alternate embodiment of the present invention.

Referring to FIG. 4 a plurality of backing members 15A–15D, includes a pair of leafs 16A and 16B, are typical of this arrangement, joined and foldable at spine 17. In the preferred embodiment of the invention, each of the plurality of backing members 15A–15D are constructed of cardboard. In the preferred embodiment, adjacent faces of sequential pair of leafs are joined by gluing. FIG. 5 shows an alternate embodiment wherein a plurality of leafs 116A–116E extend directly from one common spine 117.

Figure 6:
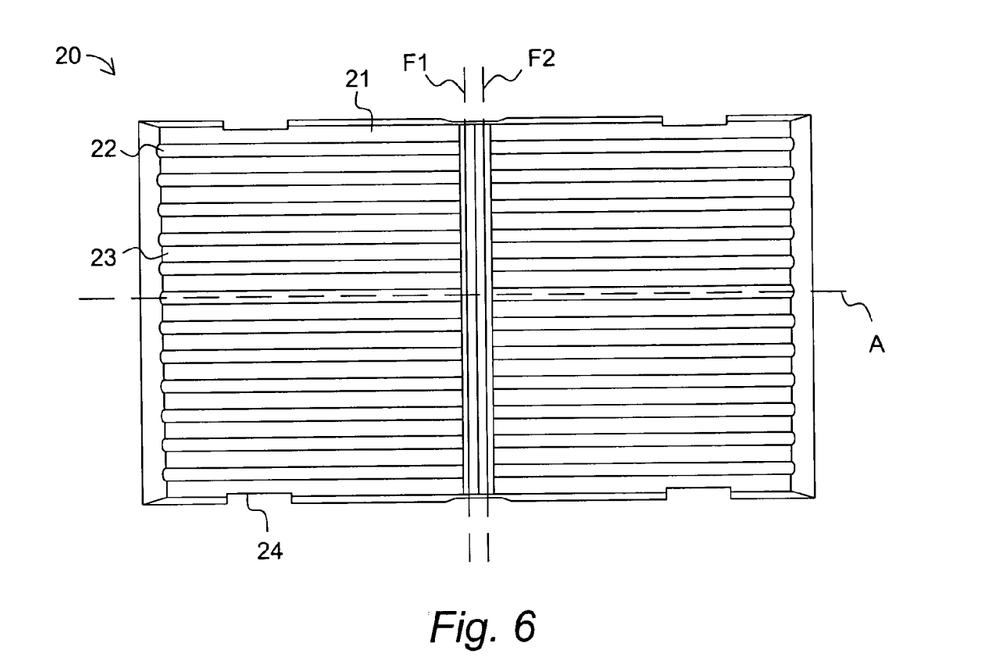
FIG. 6 is a representative top view of a nesting substrate according to a preferred embodiment of the present invention.
Figure 7:
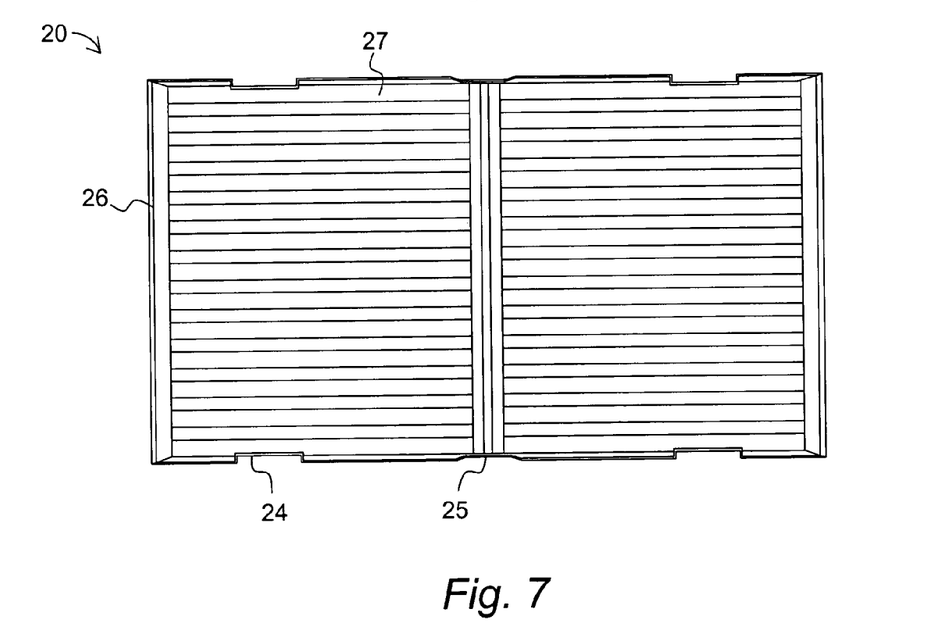
FIG. 7 is a representative bottom view of a nesting substrate according to a preferred embodiment of the present invention.

Referring to FIG. 6, nesting substrate 20 is shown to advantage. Nesting substrate 20, includes a front face 21 having a plurality of grooves 22 and ridges 23 formed thereon. Each groove 22 includes a longitudinal axis A extending along the length of each groove 22. Each nesting substrate 20 is foldable along fold line F1 and F2. Referring to FIG. 7, nesting substrate 20 includes back face 27 which is defined about an outer periphery by flange 26. Reduced section 25 facilitates folding of nesting substrate 20. As shown in FIGS. 6 and 7, nesting substrate 20 includes a backing member engagement element 24 which engages backing member 15A, shown in FIG. 1, against back face 27 of nesting substrate 20.

In the preferred embodiment, each of the nesting substrates 20 are formed of a molded fibrous pulp product. In one process, water is added to paper producing a slurry having a low solids content, i.e. 2%–10%, and preferably a 4% solids content. Preserving and conditioning additives may be added to the slurry. Once the slurry is prepared, it is applied to preformed molds and dried forming the nesting substrates 20. Plastics, synthetics or other moldable materials, may be used to form nesting substrates 20, however, a molded fibrous pulp product is preferred because of its relatively low costs of material and manufacture and its acceptability to nesting hymenoptera.

Figure 8:
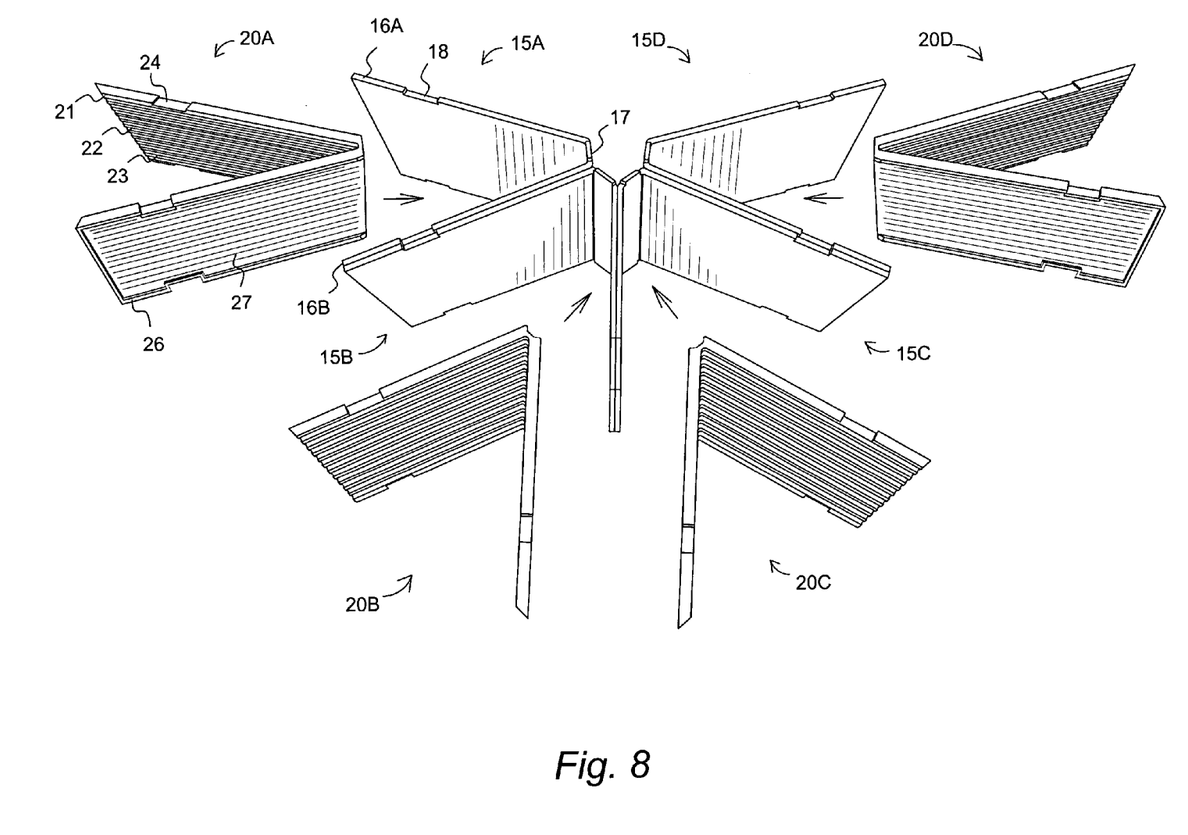
FIG. 8 is representative partially exploded perspective view of a modular cavity nest according to a preferred embodiment of the present invention.

FIG. 8, shows how a plurality nesting substrates 20A–20D are fit with respect to the plurality of backing members 15A–15D. As shown, backing member 15A, which is typical of backing members 15B–15D, includes a pair of opposing leafs 16A and 16B joined at spine 17. The plurality of nesting substrates 20A–20D, include a front face 21 having a plurality of grooves 22 and ridges 23 formed thereon and a back face 27 which is defined about an outer periphery by flange 26. The plurality of nesting substrates 20A–20D, are removably fit between adjacent leafs, in this case, nesting substrate 20A is fit between opposing leafs 16A and 16B. Flange 26 is configured such that when the plurality of nesting substrates 20A–20D are positioned against the plurality of backing members 15A–15D, the plurality of backing members 15A–15D are set within the flange 26 and are not revealed, see FIG. 1. Referring to nesting substrate 20A, it will be seen that each nesting substrate includes a one or more backing member engagement elements 24, about which one or more backing member retainers 18 of backing member 15A are positioned.

Figure 9:
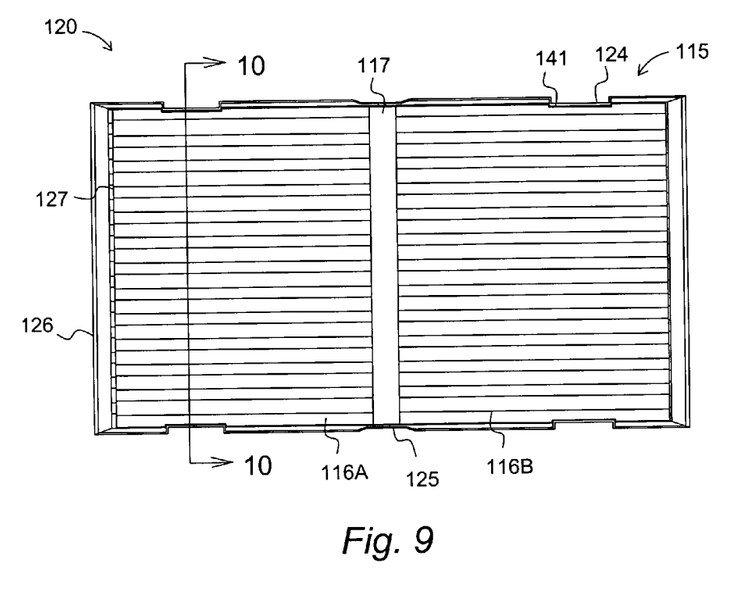
FIG. 9 is a representative bottom view of a nesting substrate and backing member according to a preferred embodiment of the present invention.
Figure 10:
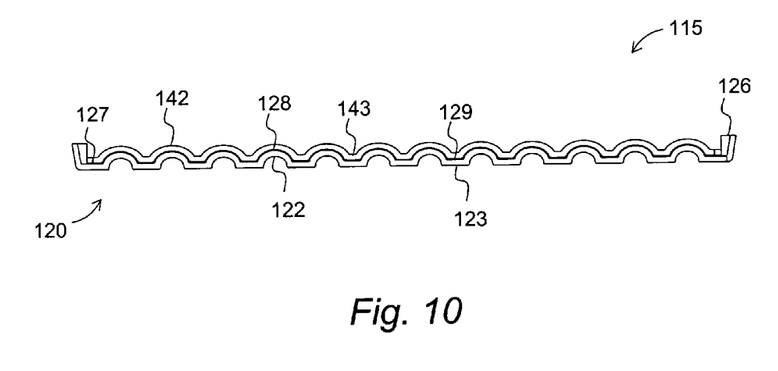
FIG. 10 is a representative end cutaway view of a nesting substrate and backing member according to a preferred embodiment of the present invention.

Referring to FIGS. 9 and 10, an alternate preferred embodiment of a nesting substrate 120 and a backing member 115 are shown in a back view and end cutaway respectively. In FIG. 9, backing member 115 is positioned on backside 127 of nesting substrate 120 within flange 126. Flange 126 includes a reduced section 125 that facilitates folding of nesting substrate 120. As seen, backing member 115 includes a pair of opposing leafs 116A and 116B joined at spine 117. FIG. 9 shows how cutout portion 141 of backing member 115 fits with respect to backing member engagement element 124 of nesting substrate 120. In FIG. 10, backing member 115 is shown positioned on backside 127 of nesting substrate 120 within flange 126. In the embodiment shown in FIGS. 9 and 10, both nesting substrate 120 and a backing member 115 are formed in a pulp molding process. As a result of the molding process, both the nesting substrate 120 and a backing member 115 may be formed including a series of undulations. On the nesting substrate 120 these are seen as a series of crests 128 and valleys 129 that correspond to the plurality of grooves 122 and ridges 123 respectively. Backing member 115 is molded to include a series of backing crests 142 and backing valleys 143 that are spaced to permit a cooperative fit of backing member 115 against the backside 127 of nesting substrate 120 such that the series of crests 128 and valleys 129 of nesting substrate 120 fit into the series of backing crests 142 and backing valleys 143. This structure eliminates the creation of spaces or cavities between nesting substrates that may be attractive as a situs for parasites, predators, nesting, or over-wintering insects, while still allowing additional insulation between individual nesting substrates.

Figure 11:
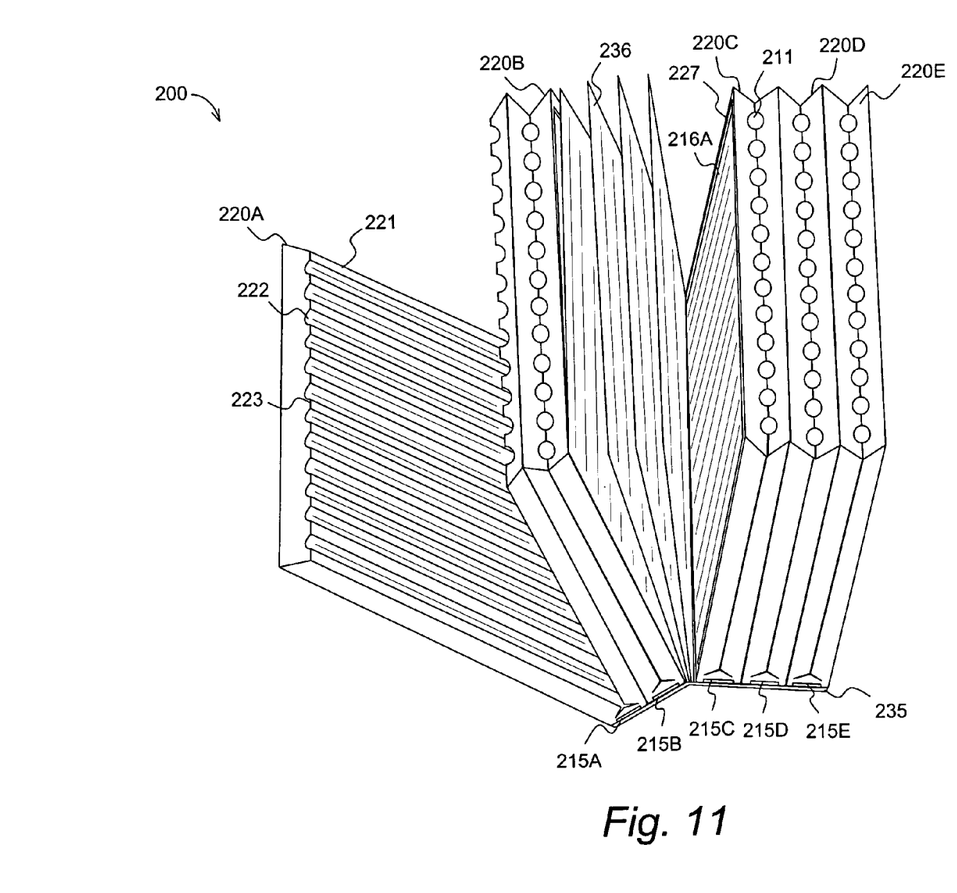
FIG. 11 is a representative perspective view of an alternate embodiment of a modular cavity nest according to a preferred embodiment of the present invention.

FIG. 11 shows an alternate preferred embodiment of modular cavity nest 200 including a plurality of nesting substrates 220A–220E. Nesting substrates 220B–220D are shown in a closed position presenting a plurality of nesting cavities 211. Nesting substrate 220A is shown in an opened configuration revealing a plurality of grooves 222 and ridges 223 formed on a first side 221 of nesting substrate 220A. FIG. 11 also shows the plurality of backing members 215A–215E against which the plurality of nesting substrates 220A–220D are positioned. Leaf 216A of backing member 215C is seen positioned within flange 227 of nesting substrate 220C. As seen in FIG. 11 backing members 215A–215E are attached to super-spine 235. In the embodiment shown in FIG. 11, one or more sheets of writing media 236 are disposed between backing members 215B–215C and bound to super-spine 235 providing a notebook where a log of nesting activity may be maintained for instance for research or educational purposes.

Figure 12:
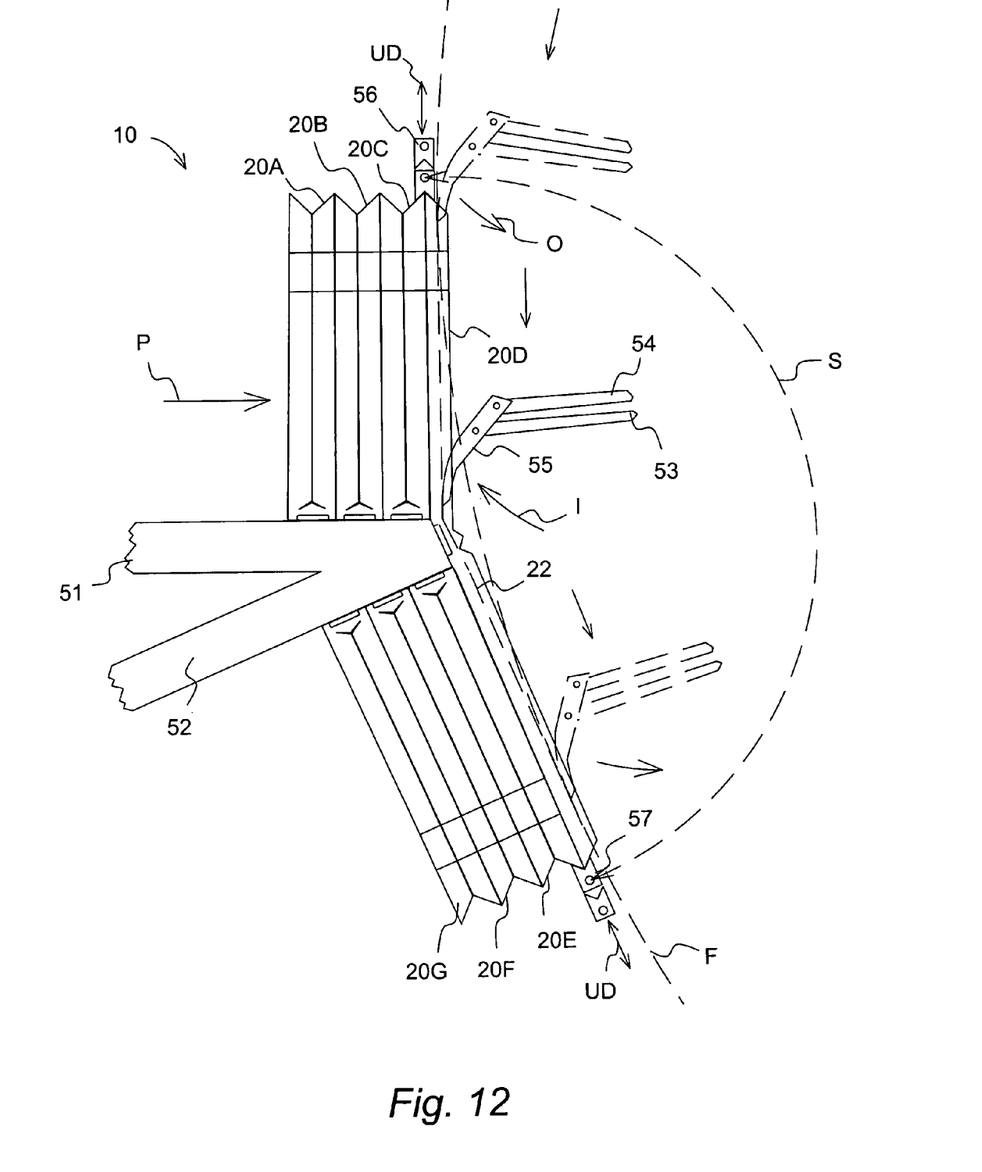
FIG. 12 is a representative side view of a modular cavity nest positioned for larvae extraction according to a preferred embodiment of the present invention.

FIG. 12 shows modular cavity nest 10 including nesting substrates 20A–20G positioned for cleaning on bench 51. Nesting substrate 20D is shown in an opened position for cleaning with keepers 56 and 57 securing portions of nesting substrates 20C and 20D and 20D and 20E respectively. Keeper 57 is movable along arc S to open a nesting substrate. Keepers 56 and 57 travel up or down, shown generally by arrows UD, in order to selectively secure or release a nesting substrate. Cleaning is effected by a plurality of fingers of which one 55 is illustrated. Each finger 55 is positioned at a distal end of an arm 53 which travels along arc F. Because the bottom of groove 22 does not follow exactly the curve of arc F, each finger 55 is adapted to maintain contact with the bottom of groove 22 by moving in or out as required to maintain such contact. Movement of each of the plurality of independent fingers, of which finger 55 is representative, may be adapted for such in and out movement, shown generally by arrows I and O, by virtue of the fact that each finger is formed of a material having an elastic nature, or by mechanical actuation and control of finger 55 by movable arm 54, or by a combination of these features. Once a given nesting substrate has been cleaned, the sensing substrate may be spray sterilized and arm 53 reverses motion to return to the an uppermost position, keeper 56 moves up, keeper 57 releases and rotates to an upper most position, modular cavity nest 10 advances in the direction of process shown by arrow P, keeper 56 moves to a down position and keeper 57 moves in a downward position to secure the uppermost edges of the following nesting substrate. Once secured, keeper 57 begins rotation along arc S to open the next nesting substrate for cleaning. Because of the relative positioning of lower bench portion 52 and the geometry of the modular cavity nest 10, as the next sequential nesting substrate is positioned for cleaning, the preceding nesting substrates advance along lower bench portion 52 in a closed and substantially inverted position. Upon completion, the modular cavity nest 10 may be secured in the closed position for reuse.

While there is shown and described the present preferred embodiment of the invention, it is to be distinctly understood that this invention is not limited thereto but may be variously embodied to practice within the scope of the following claims.

What is claimed is:

1. A nesting substrate for a modular cavity nest for hymenoptera, the nesting substrate comprising a plurality of grooves formed on a first face, the plurality of grooves forming a plurality of nesting cavities when the nesting substrate is folded along a line substantially perpendicular to an axis of one of the plurality of grooves, each of the plurality of nesting cavities including a blind end when the nesting substrate is folded along a line substantially perpendicular to an axis of one of the plurality of grooves.

2. A modular nest comprising:
   a backing member including a pair of leafs connected to a spine;
   a nesting substrate including a plurality of grooves formed on a first face, the plurality of grooves forming a plurality of nesting cavities when the nesting substrate is folded along a line substantially perpendicular to an axis of one of the plurality of grooves, the nesting substrate removably inserted between the pair of leafs of the backing member; wherein
   the nesting substrate is removably inserted between the pair of leafs of the backing member; and
   a nest closure member adapted for selective engagement for holding the backing member and the nesting substrate in a closed position wherein the plurality of grooves form the plurality of nesting cavities and an open position wherein the nesting substrate is laid open and the plurality of grooves are exposed.

3. The modular nest of claim 2 wherein the backing member further comprises a molded material.

4. The modular nest of claim 2 wherein the backing member further comprises cardboard.

5. The modular nest of claim 2 wherein the nesting substrate further comprises a molded material.

6. The modular nest of claim 2 wherein the nesting substrate further comprises a molded fibrous material.

7. The modular nest of claim 2 wherein the nesting substrate further comprises a molded pulp material.

8. A modular nest comprising:
   a plurality of backing members, each of the plurality of backing members including a pair of leafs connected to a spine;
   a plurality of nesting substrates, each of the plurality of nesting substrates including a plurality of grooves formed on a first face, the plurality of grooves forming a plurality of nesting cavities when the nesting substrate is folded along a line substantially perpendicular to an axis of one of the plurality of grooves, each of the plurality of nesting substrates is removably inserted between one of the pair of leafs of the plurality of backing members; and
   a nest closure member adapted for selective engagement for holding the plurality of backing members and the plurality of nesting substrates in a closed position wherein the plurality of grooves form the plurality of nesting cavities and an open position wherein the plurality of nesting substrates are laid open and the plurality of grooves are exposed.

9. The modular nest of claim 8 wherein the plurality of backing members further comprises a molded material.

10. The modular nest of claim 8 wherein each of the plurality of backing members further comprise a sheet of cardboard.

11. The modular nest of claim 8 wherein the plurality of molded nesting substrates further comprise a molded fibrous material.

12. The modular nest of claim 8 wherein the plurality of molded nesting substrates further comprise a molded pulp material.

13. The modular nest of claim 8 wherein the molded material further comprises a molded synthetic material.

14. The modular nest of claim 8 further comprising one or more sheets of a writing media disposed between two of the plurality of nesting substrates.

15. A modular nest comprising:
a super-spine;
a plurality of backing members, each of the plurality of backing members including a pair of leafs connected to a spine, the spine of each of the plurality of backing members attached to the super-spine;
a plurality of nesting substrates, each of the plurality of nesting substrates removably positioned between a pair of leafs of one of the plurality of backing members, each of the plurality of nesting substrates including a plurality of grooves formed therein, the plurality of grooves forming a plurality of nesting cavities when the nesting substrate is folded along a line substantially perpendicular to an axis of one of the plurality of grooves, each of the plurality of nesting cavities including a blind end when the nesting substrate is folded along a line substantially perpendicular to an axis of one of the plurality of grooves;
a nest closure member adapted for selectively maintaining the nesting substrates in a closed position wherein the plurality of grooves form the plurality of nesting cavities and an open position wherein the nesting substrate is laid open and the plurality of grooves are exposed.

16. The modular nest of claim 15 wherein each of the plurality of backing members further comprises a molded material.

17. The modular nest of claim 15 wherein each of the plurality of backing members further comprises a sheet of cardboard.

18. The modular nest of claim 15 wherein each of the plurality of nesting substrates further comprises a molded pulp material.

19. The modular nest of claim 15 further comprising one or more sheets of a writing media disposed between two of the plurality of backing members.

* * * * *